Sept. 10, 1974 A. W. FISCHER Plant Pat. 3,613
AFRICAN VIOLET
Filed May 3, 1973
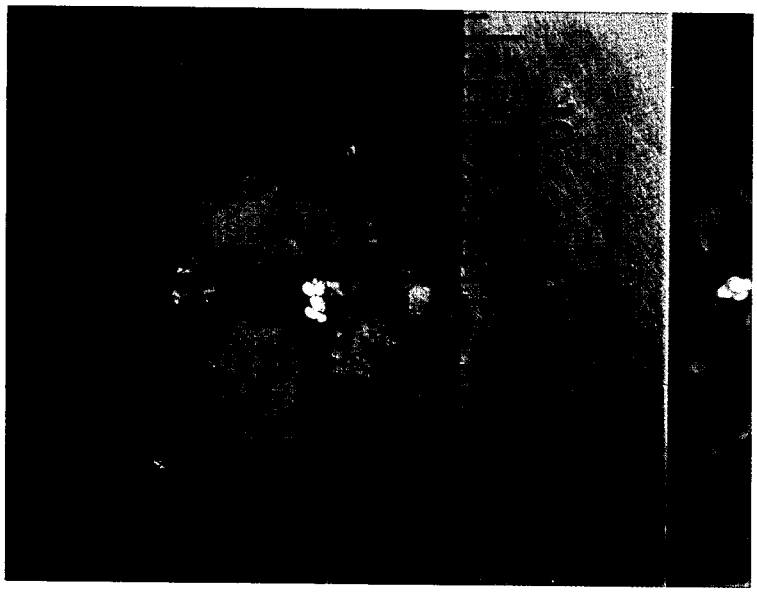
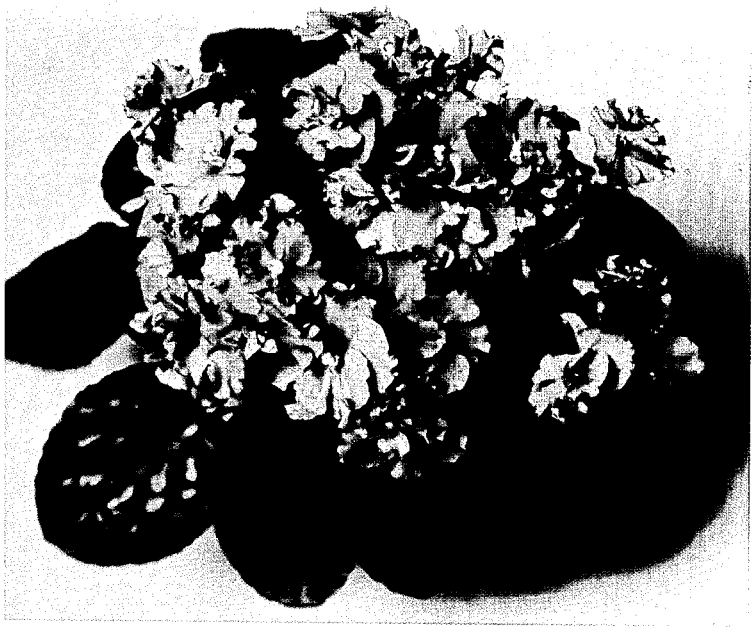

United States Patent Office

Plant Pat. 3,613
Patented Sept. 10, 1974

3,613

AFRICAN VIOLET

Arnold W. Fischer, Isernhagen, Germany, assignor to Geo. J. Ball, Inc., West Chicago, Ill.

Filed May 3, 1973, Ser. No. 357,076
Int. Cl. A01h *5/00*
U.S. Cl. Plt.—69 1 Claim

ABSTRACT OF THE DISCLOSURE

A new variety of African violet plant distinguished by the unique purple-pink coloring of its blossoms which tend to cluster at the center of the plant to present an attractive and showy appearance, the bright flower colors contrasting with a surrounding display of abundant foliage, and the flowers appearing high above the foliage on sturdy upright stems.

Background of the New Plant

My new variety of African violet plant originated as a seedling in my glass houses at Isernhagen, Germany, and is the result of a crossing made by me with the objective of producing an improved pink African violet plant having better growing and flowering habits, the parents of this new variety having been selected by me from among my breeding stock at Isernhagen with the said objective in mind. This seedling was selected for propagation and test because it best exhibited the characteristics I was seeking and asexual reproduction of this variety carried on by me through successive generations by means of leaf cuttings has shown the desired features to be firmly fixed and to hold true. This fact has now been affirmed by commercial scale propagation being carried on at West Chicago, Illinois, U.S.A., by means of division of shoots and by leaf cuttings.

Description of the Drawing

My new variety of African violet plant is illustrated by the accompanying full color photographic drawing in which the upper view is a close-up of a typical blossom showing its form and size and the lower view shows the new plant in full bloom, the color rendition being as nearly true as is reasonably possible to obtain by conventional photographic procedures. The true colors are shown by the painted color patches affixed to the drawing at the bottom portion thereof, the patch A being of the color of the yung mature bloom and the patch B being of the color of an older flower.

Description of the New Plant

The following is a detailed description of my new African violet plant with color designations according to the Horticultural Colour Chart created by Robert F. Wilson and adopted by the British Colour Council and The Royal Horticultural Society at London, England.

THE PLANT

Origin: Seedling
Parentage:
- *Seed Parent.*—X69–25, an unnamed and unpatented shell pink and frilled variety.
- *Pollen Parent.*—069–13, an unnamed and unpatented red single.

Both parents were selected by me from among my stock maintained for breeding purposes at Isernhagen, Germany.

Classification:
- *Botanic.*—*Saintpaulia ionantha.*
- *Commercial.*—African Violet for potting.

Form: Compact potted plant.

Height: 3½ to 4 inches from soil to top of flower.
Growth: Sturdy and condensed.
Strength: Good. Fairly strong petioles, which tend to spread horizontally.
Foliage: Quantity—Abundant.
- *Size of Leaf.*—About 2¼ inches long x 2¼ inches wide.
- *Shape of Leaf.*—Ovate to orbicular with crenate margins.
- *Texture.*—Tomentose.
- *Ribs and Veins.*—Pinnately veined (pronounced on under side of leaf).
- *Color.*—Upper side—Parsley Green 00962. Under Side—Pansy Violet 033 fading to Pastel Mauve 433.
- *Petioles.*—Length varies with age of plant, about 2½ inches long on mature leaf.

THE BUD

Form: Globular, becoming urn-shaped as it opens.
Size: About ¼ inch in diameter just before opening.
Opening Rate: Very slow. Five weeks from visible bud to opening of flower.
Color: Lilac Purple 031 and 031/3 when petals begin to unfurl.
Sepals: Enclose the bud for a very short time.
- *Form.*—Spear shaped, unbranched and upstanding.
- *Color.*—*Inside*—Maroon 1030/3. Outside—Maroon 1030.

Calyx: Shape—Funnel-shaped and synsepalous.
- *Splitting.*—Calyx splits to star shape.
- *Aspect.*—Smooth on inside. Hairy on outside.

Peduncle: Length—About 2½ inches.
- *Strength.*—Flexible and erect.
- *Aspect.*—Very tomentose.
- *Color.*—Pod Green 061/2 with Maroon.

THE FLOWER

Blooming Habit: Profuse and recurrent the year around.
Size of Flower: Medium. Diameter: 1⅜ inches.
Shape of Flower: Very open cup-shaped when first opening, becoming flat when fully opened.
Borne: The inflorescence of this plant is a cyme.
Petalage: Five petals, three larger than remaining two.
- *Arrangement.*—Sympetalous.
- *Form.*—Orbicular with bilateral symmetry and frilled, undulated margins.
- *Color.*—Top side of petals: Young mature bloom—Doge Purple 732/1; old flower—Petunia Purple 32/1 with center of more intense Petunia Purple 32. Reverse side of petals—Phlox Purple 632/1.
- *Texture.*—Soft.
- *Appearance.*—Glittery on upper surface, satiny on under surface.

Peduncle: Length 2½ inches. Pedicles—1 to 1½ inches long.
- *Strength.*—Sturdy and upright.
- *Color.*—Pod Green 061/2.

Discoloration: After full bloom, color tends to fade.
Effect of Weather: Hot weather suppresses flowering and fades the color. This plant thrives in 80% to 90% humidity.
Fragrance: None.
Persistence: Flowers hang on and dry.
Lasting Quality: 14 to 18 days for fully opened flower.

REPRODUCTIVE ORGANS

Stamens:
- *Anthers.*—Two (each composed of two anther cells), Sulphur Yellow 1 in color, in basified arrangement, and 1/16 inch long.
- *Filaments.*—⅛ inch long. Color—Petunia Purple 32/1.

*Pollen.*—Color—White.

Pistils: One only.

*Style.*—5/16 inch long. Color—Phlox Purple 532/3.

*Stigma.*—Color—Phlox Purple 632/1.

Ovaries: Tomentose and superior.

This new variety of African violet plant is particularly notable for the intensity and brightness of its flower coloring and its attractive evenly growing foliage which tends to spread radially outward from the flowers tending to cluster at the center of the plant and which stand above the foliage to provide a very showy display. The plant is a vigorous grower with an abundant production of blossoms which bloom recurrently the year around, thereby providing an unusually attractive house plant.

I claim:

1. A new variety of African violet plant, substantially as herein shown and described, characterized by its profuse production of showy purple-pink blossoms which tend to cluster at the center of the plant and above a rotate display of abundant foliage; and by its vigorous growth and recurrent blooming habit.

No references cited.

ROBERT E. BAGWILL, Primary Examiner